United States Patent
Ando et al.

(10) Patent No.: US 9,302,023 B2
(45) Date of Patent: Apr. 5, 2016

(54) ALDEHYDE GAS DEODORANT AND METHOD FOR PRODUCING SAME

(71) Applicant: TOAGOSEI CO., LTD., Tokyo (JP)

(72) Inventors: Satoko Ando, Nagoya (JP); Koji Sugiura, Nagoya (JP)

(73) Assignee: TOAGOSEI CO., LTD., Tokyo (JP)

( * ) Notice: Subject to any disclaimer, the term of this patent is extended or adjusted under 35 U.S.C. 154(b) by 92 days.

(21) Appl. No.: 14/377,540

(22) PCT Filed: Feb. 5, 2013

(86) PCT No.: PCT/JP2013/052597
§ 371 (c)(1),
(2) Date: Aug. 8, 2014

(87) PCT Pub. No.: WO2013/118714
PCT Pub. Date: Aug. 15, 2013

(65) Prior Publication Data
US 2015/0023903 A1     Jan. 22, 2015

(30) Foreign Application Priority Data

Feb. 9, 2012   (JP) ................. 2012-025998

(51) Int. Cl.
*A61L 9/01* (2006.01)
*C08G 18/60* (2006.01)
*D06M 13/422* (2006.01)

(52) U.S. Cl.
CPC ............... *A61L 9/01* (2013.01); *D06M 13/422* (2013.01)

(58) Field of Classification Search
None
See application file for complete search history.

(56) References Cited

U.S. PATENT DOCUMENTS

2010/0297053 A1* 11/2010 Hirukawa ................. A61L 9/01
424/76.01

FOREIGN PATENT DOCUMENTS

| JP | 51-44587 | | 4/1976 | |
|---|---|---|---|---|
| JP | 9-173830 | A | 7/1997 | |
| JP | 2000-279500 | A | 10/2000 | |
| JP | 2003-335784 | A | 11/2003 | |
| JP | 2004-24330 | A | 1/2004 | |
| JP | 2007-167495 | A | 7/2007 | |
| JP | 2008-178788 | A | 8/2008 | |
| JP | 2010-125401 | A | 6/2010 | |
| JP | 2010-240332 | A | 10/2010 | |
| JP | 2010-253409 | A | 11/2010 | |
| JP | 2011-130865 | A | 7/2011 | |
| WO | WO 2004/058311 | A1 | 7/2004 | |
| WO | WO 2007/088879 | A1 * | 8/2007 | ........... A61L 9/01 |

OTHER PUBLICATIONS

International Search Report, issued in PCT/JP2013/052597, dated Apr. 16, 2013.

* cited by examiner

*Primary Examiner* — Jeffrey T Palenik
(74) *Attorney, Agent, or Firm* — Birch, Stewart, Kolasch & Birch, LLP

(57) ABSTRACT

To provide a method for producing an aldehyde gas deodorant which has high aldehyde deodorizing performance, and which is negative for mutagenicity and excellent in safety, and a deodorant processed product.

A method for producing an aldehyde gas deodorant, the method comprises the steps of: preparing a deodorizing composition containing a dihydrazide compound, a water-containing inorganic powder, and water; and heating the deodorizing composition at a temperature of from 45° C. to 90° C. so that water remains in an amount of 4.5% by mass or more, based on the total mass of the deodorant produced, and wherein the aldehyde gas deodorant is negative for mutagenicity measured by an AMES test.

14 Claims, No Drawings

ALDEHYDE GAS DEODORANT AND METHOD FOR PRODUCING SAME

TECHNICAL FIELD

The present invention relates to a deodorant comprising a dihydrazide compound and a water-containing inorganic powder having supported thereon the dihydrazide compound, which has high deodorizing ability with respect to aldehyde gas, and which is negative for mutagenicity, and a method for producing the same. The deodorant of the present invention can be used in the application in which it is necessary to care about the safety, such as fiber products used in a living space.

BACKGROUND ART

In recent years, as seen in a sick house/sick building syndrome and the like, a damage to person's health due to formaldehyde or the like has attracted attention. It is known that, as a method for removing aldehyde gas in an indoor environment, an aldehyde removing agent comprising an amine compound is effective. Aldehyde gas is a collective name covering aldehyde compounds volatile at normal temperature, including formaldehyde and acetaldehyde as representative examples.

For example, Patent Document 1 discloses that exhaust gas containing aldehyde gas is contacted with a liquid having an amine compound dissolved therein to remove aldehyde gas in the exhaust gas. However, an amine compound in the liquid state has a strong unpleasant odor, and therefore is unsuitable for the application to a daily life, such as a living space including, for example, a living room or a kitchen.

For solving the above problem, an aldehyde gas absorbent comprising an amine compound and an inorganic material having supported thereon the amine compound has been known, and Patent Document 2 discloses a deodorizing adsorbent comprising an amino group-containing silane coupling agent and a porous metal oxide, such as silica, alumina, titania, or zirconia, having supported thereon the silane coupling agent and has a description that the adsorbent can be used in a filter for an air cleaner or the like. In the working Examples, there is a description showing that the silane coupling agent was supported on a silica carrier and subjected to evaporation to dryness at 120° C., but the aldehyde deodorizing ability is not satisfactory.

Further, Patent Document 3 discloses an aminoguanidine compound as a chemical agent for removing an aldehyde. However, the aminoguanidine compound is in the form of a hydrochloride or sulfate which is a strong acid, and hence has problems in that when such a strongly acidic compound is in contact with a metal during the processing or use thereof, the metal suffers corrosion, and in that when the acidic compound is spread using a binder, discoloration occurs.

A number of aldehyde gas deodorants have been proposed in which the deodorants comprise a hydrazine compound as a compound which is almost neutral and is easily reacted with an aldehyde, and an inorganic compound carrier having supported thereon the hydrazine compound. For example, Patent Document 4 discloses an aldehyde gas deodorant comprising hydrated hydrazine and porous silicon dioxide or aluminum silicate having supported thereon the hydrated hydrazine. Further, Patent Document 3 discloses an aldehyde gas deodorant obtained by supporting succinic dihydrazide, carbohydrazide, or oxalic dihydrazide on aluminum silicate and magnesium silicate by heating at 140° C. to 220° C. These aldehyde gas deodorants comprising a hydrazine compound and an inorganic compound having supported thereon the hydrazine compound are excellent in processability and aldehyde deodorizing effect; however, these deodorants do not satisfactorily care about the safety of a human body.

Specifically, the above Patent Documents have no description about the mutagenicity with respect to the above-mentioned aldehyde gas deodorants. It is known that, for example, hydrated hydrazine itself is a substance which is strongly positive for mutagenicity. Therefore, the aldehyde gas deodorant using such a hydrazine is considered to be positive for mutagenicity, and is not regarded as a satisfactorily safe aldehyde gas deodorant to be used in a living space. On the other hand, with respect to succinic dihydrazide, it is known that the substance itself is weakly positive for mutagenicity, and it has been considered that succinic dihydrazide is acceptable as an aldehyde gas deodorant used in a living space. However, the present inventors have found the problem that when an inorganic compound carrier having succinic dihydrazide supported thereon is heated, the mutagenicity becomes positively increased.

Further, it has been known that, among the hydrazine compounds as a chemical agent for removing an aldehyde, carbohydrazide, oxalic dihydrazide, and adipic dihydrazide are negative for mutagenicity. For example, Patent Document 5 discloses an aldehyde gas deodorant obtained by mixing 40 g of adipic dihydrazide in the form of an aqueous solution with 80 g of silica or alumina particles and then drying the resultant mixture at 80° C. for 12 hours to evaporate water. Patent Document 6 discloses a deodorant using no succinic dihydrazide, and containing 4 to 12% by mass of carbohydrazide and/or adipic dihydrazide, 1 to 5% by mass of hydroxylamine sulfate, 0.1 to 0.5% by mass of smectite, and 82.5 to 94.9% by mass of water. Patent Document 6 discloses that the reason why succinic dihydrazide is not used is that it contains a large amount of hydrazine, which is positive for mutagenicity, as an impurity. The present inventor has found a problem in that even when the organic acid dihydrazide is negative for mutagenicity, an inorganic compound carrier having supported thereon the dihydrazide may be positive for mutagenicity.

With respect to a deodorant which undergoes a chemical reaction with an aldehyde to exhibit a deodorizing function, such as a hydrazine compound, when the deodorant is solely used, the efficiency of contact of the deodorant with aldehyde gas is low so that the deodorant cannot exhibit high deodorizing performance. Therefore, a method has been proposed in which the deodorant is supported on various inorganic compounds so that the deodorant easily exhibits aldehyde deodorizing performance. However, it has not been known that there is a possibility that, in the inorganic compound carrier having supported thereon the hydrazine compound which itself is negative for mutagenicity, a part of the hydrazine compound is decomposed due to the carrier used or the supporting conditions during the step for supporting, so that the mutagenicity becomes positive.

In the end use of the above aldehyde gas deodorants, there are many products that a person in a living space is frequently in contact with in a daily life, for example, fiber products, e.g., clothes and bedding for preventing a body odor of aged person, such as nonenal, a car mat for preventing VOC, and interior products for preventing tobacco odor. Further, there is a possibility that even a product to be incorporated into an apparatus, such as a filter for an air conditioner, is in contact with a human body when replacing the filter with another, or fibers constituting the filter are removed and blown away and inhaled by a human body and hence, similarly, there should be the consideration of the safety. Therefore, an aldehyde gas deodorant, which has high aldehyde deodorizing performance and which is negative for mutagenicity, is desired, but an aldehyde gas deodorant which satisfies the requirement has not yet been obtained.

PRIOR ART DOCUMENT

Patent Document

Patent Document 1: JP-A-51-44587 (JP-A denotes a Japanese unexamined patent application publication)
Patent Document 2: JP-A-9-173830
Patent Document 3: WO 2004/058311
Patent Document 4: JP-A-2004-24330
Patent Document 5: JP-A-2007-167495
Patent Document 6: JP-A-2011-130865

DISCLOSURE OF THE INVENTION

Problems to be Solved by the Invention

It is an object of the present invention to provide an aldehyde gas deodorant which has high deodorizing performance with respect to aldehyde gas, and which is negative for mutagenicity and excellent in safety, and to provide a deodorant processed product in the form of a fiber, a coating composition, a sheet, a shaped article, or the like, which exhibits excellent deodorizing performance using the above deodorant.

Means for Solving the Problems

The present inventors have found that a deodorant, which is produced by a method in which a dihydrazide compound, a water-containing inorganic powder, and water are mixed together and heated at a temperature of from 60° C. to 90° C. so that water remains in an amount of 4.5% by mass or more, based on the total mass of the deodorant produced, has high deodorizing performance with respect to aldehyde gas and is negative for mutagenicity measured by an AMES test, and have found that a deodorant processed product can be obtained using the deodorant.

The means for solving the above-mentioned problems are specifically shown below.

<1> A method for producing an aldehyde gas deodorant comprising the steps of: preparing a deodorizing composition containing a dihydrazide compound, a water-containing inorganic powder, and water; and heating the deodorizing composition at a temperature of from 45° C. to 90° C. so that water remains in an amount of 4.5% by mass or more, based on the total mass of the deodorant produced, and wherein the aldehyde gas deodorant is negative for mutagenicity measured by an AMES test;

<2> the method for producing an aldehyde gas deodorant according to item <1> above, wherein the dihydrazide compound is represented by the formula (1) below:

$$H_2NHN—X—NHNH_2 \quad (1)$$

wherein X represents a group (—CO—) or a group (—CO-A-CO—) wherein A represents an alkylene group having 1 to 16 carbon atoms or an arylene group having 6 to 12 carbon atoms;

<3> the method for producing an aldehyde gas deodorant according to item <1> or <2> above, wherein the dihydrazide compound is at least one selected from the group consisting of carbohydrazide, succinic dihydrazide, adipic dihydrazide, and isophthalic dihydrazide;

<4> the method for producing an aldehyde gas deodorant according to any one of items <1> to <3> above, wherein the water-containing inorganic powder independently has a water content of 3 to 25% by mass under 1 atm at 25° C.;

<5> the method for producing an aldehyde gas deodorant according to any one of items <1> to <4> above, wherein the water-containing inorganic powder is amorphous;

<6> the method for producing an aldehyde gas deodorant according to any one of items <1> to <5> above, wherein the water-containing inorganic powder is an amorphous composite oxide;

<7> the method for producing an aldehyde gas deodorant according to any one of items <1> to <6> above, wherein the water-containing inorganic powder is a composite oxide containing an oxide selected from the group consisting of $Al_2O_3$, $SiO_2$, $MgO$, $CaO$, $SrO$, $BaO$, $ZnO$, $ZrO_2$, $TiO_2$, $WO_2$, $CeO_2$, $Li_2O$, $Na_2O$, and $K_2O$;

<8> the method for producing an aldehyde gas deodorant according to any one of items <1> to <7> above, wherein the water-containing inorganic powder comprises the formula: $X_2O—Al_2O_3—SiO_2$, wherein X represents at least one alkali metal selected from Na, K, and Li;

<9> the method for producing an aldehyde gas deodorant according to any one of items <1> to <8> above, wherein the amount of the dihydrazide supported is 10 to 90% by mass, based on the total mass of the dihydrazide compound and the water-containing inorganic powder;

<10> the method for producing an aldehyde gas deodorant according to any one of items <1> to <9> above, wherein the dihydrazide compound comprises adipic dihydrazide;

<11> an aldehyde gas deodorant which is obtained by the method according to any one of items <1> to <10> above;

<12> a deodorant processed product comprising the aldehyde gas deodorant according to item <11> above;

<13> the deodorant processed product according to item <12> above, which is selected from the group consisting of a fiber, a coating composition, a sheet, and a shaped article;

<14> the deodorant processed product according to item <13> above, which is obtained by subjecting the aldehyde gas deodorant to after-processing using a binder.

MODES FOR CARRYING OUT THE INVENTION

Hereinbelow, the present invention will be described in detail. "%" indicates % by mass, and "part(s)" indicates part(s) by mass unless otherwise specified. The aldehyde gas deodorant of the present invention comprises a dihydrazide compound and a water-containing inorganic powder having supported thereon the dihydrazide compound, and is characterized by having a water content of 4.5% by mass or more, based on the total mass of the deodorant, and being negative for mutagenicity. Such an aldehyde gas deodorant can be obtained by, for example, mixing together a dihydrazide compound, a water-containing inorganic powder, and water and heating the resultant mixture at 45° C. to 90° C.

Dihydrazide Compound

The dihydrazide compound in the present invention is a hydrazine compound having two hydrazino groups in the molecule thereof.

As a specific example of the dihydrazide compound used in the present invention, there can be mentioned a dihydrazide compound represented by the following general formula:

$$H_2NHN—X—NHNH_2 \quad (1)$$

wherein X represents a group (—CO—) or a group (—CO-A-CO—) wherein A represents an alkylene group having 1 to 16 carbon atoms or an arylene group having 6 to 12 carbon atoms.

In the general formula (1) above, preferred examples of alkylene groups represented by A include linear alkylene groups having 1 to 12 carbon atoms, such as a methylene group, an ethylene group, a trimethylene group, a tetramethylene group, a pentamethylene group, a hexamethylene group, a heptamethylene group, an octamethylene group, a nonamethylene group, a decamethylene group, and an undecamethylene group. Among the alkylene groups, the alkylene group is preferably a linear alkylene group having 1 to 4 carbon atoms. Examples of a substituent for the alkylene group include a hydroxyl group. Examples of arylene groups include a phenylene group, a biphenylene group, a naphthylene group, an anthrylene group, and a phenanthrylene group, and, among the arylene groups, preferred are a phenylene group, a naphthylene group, and the like. Examples of a substituent for the arylene group include a group as the same as the above-mentioned substituent for the alkylene group.

Specific examples of dihydrazide compounds of the general formula (1) above include dibasic acid dihydrazides, such as carbohydrazide (which is also called carbonic dihydrazide), oxalic dihydrazide, malonic dihydrazide, succinic dihydrazide, glutaric dihydrazide, adipic dihydrazide, azelaic dihydrazide, sebacic dihydrazide, 2-dodecanedioic dihydrazide, maleic dihydrazide, fumaric dihydrazide, diglycolic dihydrazide, tartaric dihydrazide, malic dihydrazide, isophthalic dihydrazide, terephthalic dihydrazide, dimer acid dihydrazide, and 2,6-naphthoic dihydrazide.

Among them, the dihydrazide compound is preferably a compound which are negative for mutagenicity and which have a smaller molecular weight because when a comparison is made between dihydrazide compounds having the same mass, it is likely that the use of the dihydrazide compound having a smaller molecular weight achieves a large deodorizing capacity. Further, it is important that the dihydrazide compound is industrially available at a low cost. From such a point of view, a preferred dihydrazide compound is at least one selected from carbohydrazide, succinic dihydrazide, adipic dihydrazide, and isophthalic dihydrazide, and further preferred is adipic dihydrazide.

In the industrial production method for a dihydrazide compound, hydrazine is frequently used as a raw material. Hydrazine is a compound which is highly positive for mutagenicity, and hence, when the raw material remains as an impurity, the resultant dihydrazide compound may be positive for mutagenicity. Therefore, in the present invention, it is preferred that a dihydrazide compound containing no hydrazine as an impurity is used.

Water-Containing Inorganic Powder

The water-containing inorganic powder used in the present invention is a powder made solely of an inorganic material containing water in the standard state. For achieving the deodorant which is negative for mutagenicity, it is necessary that the water content of the aldehyde gas deodorant comprising the water-containing inorganic powder having supported thereon a dihydrazide compound be 4.5% by mass or more, and there is a need to select the dihydrazide compound and water-containing inorganic powder and select the supporting method so that the aldehyde gas deodorant has a water content of 4.5% by mass or more in air at room temperature. With respect to the water content of the water-containing inorganic powder to be selected, when using the water-containing inorganic powder which independently has a large water content, the resultant aldehyde gas deodorant is likely to exhibit excellent deodorizing performance. However, when using the water-containing inorganic powder which independently has too large a water content, the relative amount of the dihydrazide compound to the resultant aldehyde gas deodorant is small, so that the deodorizing capacity is disadvantageously reduced. Therefore, generally, the water-containing inorganic powder used in the present invention independently advantageously has a water content in the standard state of 3 to 25% by mass, preferably 4 to 20% by mass, more preferably 5 to 15% by mass. Further, it is necessary that the deodorant having supported thereon a dihydrazide compound have a water content in the standard state of 4.5% by mass or more, based on the total mass of the deodorant. The term "standard state" means 1 atm at 25° C.

The water-containing inorganic powder used in the present invention is preferably amorphous because high aldehyde deodorizing capacity can be achieved. The term "amorphous" means that an apparent diffraction signal caused by a crystal plane is not recognized in the measurement of powder X-ray diffraction, specifically means that, in an X-ray diffraction pattern obtained by plotting diffraction angles on the abscissa and diffraction signal intensities on the ordinate, almost no signal peak having high sharpness (so-called sharp peak) appears. The reason that the amorphous water-containing inorganic powder is preferred in the construction in the present invention is presumed as follows. In a crystalline water-containing inorganic powder, the crystal structure limits the pores in the powder, so that diffusion is unlikely to occur upon supporting a dihydrazide compound on the powder. Therefore, the crystalline water-containing inorganic powder having supported thereon a dihydrazide compound is unlikely to exhibit aldehyde deodorizing performance, as compared to an amorphous water-containing inorganic powder having supported thereon the same dihydrazide compound.

With respect to the particle size of the water-containing inorganic powder used in the present invention, there is no particular limitation, but the particle size of the water-containing inorganic powder reflects the particle size of the deodorant. Therefore, the larger particles are unlikely to suffer aggregation and hence easily dispersed when used in products of application, and, on the other hand, the smaller particles are easily processed into various products, such as a fiber product using thin fibers, and have also an advantage in that, for example, the smaller particles are unlikely to be removed after processed. For these reasons, with respect to the preferred particle diameter, a median diameter is preferably 0.1 to 100 μm, as measured by a laser diffraction-type particle size distribution measurement apparatus, more preferably 0.5 to 20 μm, yet more preferably 2 to 10 μm.

With respect to the specific component of the water-containing inorganic powder used in the present invention, there is no particular limitation, and examples include silica gel, water-containing aluminum oxide, water-containing magnesium oxide, water-containing titanium oxide, water-containing zirconium oxide, water-containing zirconium hydroxide, zirconium phosphate, titanium phosphate, aluminum phosphate, hydrotalcite, various types of zeolite, various types of composite oxides, and various types of clay compounds. Preferred are composite oxides comprising $Al_2O_3$, $SiO_2$, MgO, CaO, SrO, BaO, ZnO, $ZrO_2$, $TiO_2$, $WO_2$, $CeO_2$, $Li_2O$, $Na_2O$, $K_2O$, or the like, and further preferred are amorphous water-containing composite oxides represented by the formula: $X_2O$—$Al_2O_3$—$SiO_2$ (wherein X represents at least one alkali metal selected from Na, K, and Li). Of these, especially preferred is the composite oxide of the above formula wherein X is Na, i.e., $Na_2O$—$Al_2O_3$—$SiO_2$ because the resultant deodorant is likely to exhibit an effect such that the aldehyde deodorizing capacity is high and the mutagenicity is negative.

The amorphous water-containing composite oxide represented by the formula: $X_2O$—$Al_2O_3$—$SiO_2$ can be synthesized by, for example, the following method. An aqueous solution of an aluminum salt and an aqueous solution of an alkali metal silicate are mixed so that the $SiO_2/Al_2O_3$ molar ratio becomes 6 or more, more preferably in the range of from 8 to 15, under conditions at room temperature under atmospheric pressure, and, if necessary, an acid or an alkali is added thereto, and the resultant mixture is matured by heating at a temperature in the range of from 40° C. to 100° C., followed by washing with water, dehydration, drying, and pulverization, thus obtaining the amorphous water-containing composite oxide.

Alternatively, the amorphous water-containing composite oxide can be synthesized by another method for synthesis in which, for example, an aqueous aluminum solution is added to colloidal silica or water glass, and further, while maintaining the pH of the system in the range of from about 3 to 7 using an acid or an alkali, the resultant mixture is satisfactorily uniformly mixed, and further heated at a temperature, for example, in the range of from 40° C. to 100° C., and is matured or is not matured, followed by washing with water, dehydration, and drying. In this case, the amounts of the silica sol and aluminum water-soluble salt used can be selected like the above-mentioned $SiO_2/Al_2O_3$ ratio. As examples of aluminum salts, there can be mentioned water-soluble salts, such as sulfates, nitrates, chlorides, iodides, and bromides. Further, as examples of alkalis or acids used in the above synthesis, there can be mentioned alkalis, such as sodium hydroxide, potassium hydroxide, sodium carbonate, and potassium carbonate, and acids, such as hydrochloric acid, sulfuric acid, and nitric acid.

The specific surface area of the water-containing inorganic powder in the present invention can be measured by a BET method in which a specific surface area is determined based on the nitrogen adsorption amount. The larger the specific surface area, the larger the contact area of the deodorant with malodorous gas, or the larger the aldehyde gas adsorption amount. In the water-containing inorganic powders having the same pore volume, the powder having a larger specific surface area means that the powder has a smaller pore diameter. When supporting a dihydrazide compound on the powder, the dihydrazide compound is easily incorporated into pores of the powder having a larger pore diameter. Therefore, there is the optimum range of the specific surface area. Specifically, the water-containing inorganic powder preferably has a specific surface area of 50 to 700 m²/g, more preferably has a specific surface area of 200 to 600 m²/g.

Further, when the average pore diameter of the water-containing inorganic powder is too large, the specific surface area is reduced, and hence the amount of the dihydrazide compound supported is reduced, so that the adsorption performance with respect to malodorous gas becomes poor. In the water-containing inorganic powder having too large an average pore diameter, when the specific surface area is satisfactorily increased, the void content of the water-containing inorganic powder becomes too large, so that the powder is reduced in mechanical strength or becomes poor in the ability to support the dihydrazide compound, leading to a problem in that decomposition easily occurs due to slight heating. The average pore diameter can be determined by making a calculation from the total pore volume and specific surface area measured by a gas adsorption method, and the water-containing inorganic powder in the present invention preferably has an average pore diameter in the range of from 5 to 25 nm, more preferably from 7 to 20 nm.

It is known that the average pore diameter (D), and the pore volume (V) and specific surface area determined by a BET method generally have therebetween the relationship represented by the following formula (2):

$$D = 4 \times V/Sc \times 10^3 \quad (2)$$

Unit: nm
(V: pore volume [ml/g]; Sc: specific surface area [m²/g])

Mutagenicity

Mutagenicity indicates properties that induce mutation at a cell or an individual level, and this term has a wide meaning covering properties which damage a gene (DNA) of a cell. The mutagenicity test is classified into three types, i.e., a gene mutation test, a chromosomal mutation test, and a test for influence on DNA, and the mutagenicity test in the present invention is a back mutation test using microorganisms (so-called an AMES test), which is classified as a gene mutation test. The AMES test is rapid, high in sensitivity, and economical and has a great amount of stored data which are available, and further has correlation with carcinogens. For this reason, the AMES test is a test method generally performed as a primary screening test. In the international standards for the AMES test, the judgment is selected from negative and positive. When the number of mutation colonies is increased 2 times or more the negative control and further the increase of the number has dependency on the concentration of the substance tested, the mutagenicity is judged to be positive. About 80 to 90% of carcinogens are positive in the AMES test, and therefore it can be expected that the substance negative in the test is probably highly not a carcinogen. All the substances positive in the AMES test are not a carcinogen, but the AMES test is an important safety test used as an index in various rules and regulations, such as Chemical Substances Control Law and Industrial Safety and Health Law.

Specifically, in the AMES test, 5 types of bacteria, i.e., *Salmonella typhimurium* (4 strains) and *Escherichia coli* (1 strain) are used. The amount of the sample of the present invention used in the AMES test, that is, the amount of the aldehyde gas deodorant tested is 5,000 mg at most, and this is appropriately diluted in several stages, and to the resultant stepwise suspension is added S9MIX (S9+), which is an S9 reagent, or a phosphate buffer (S9−), and further each of the bacteria is added in a predetermined amount to the resultant mixture, and then shaken at 70 rpm at 37° C. for 20 minutes to effect pre-incubation. S9 is a reagent obtained by grinding liver of a rat and subjecting it to centrifugal separation (centrifugal force: 9,000 G), and adding to the resultant supernatant (S-9: which contains a metabolic enzyme) a coenzyme required (Cofactor-I). There are some chemical substances that exhibit mutagenicity only after metabolized in a human body, and some substances that exhibit mutagenicity before metabolized rather than after metabolized, and therefore, in the AMES test, both of them are tested. Then, 2 ml of a top agar made of agar containing sodium chloride and biotin or histidine is added to the above mixture and well stirred, and then laid on a minimum glucose agar medium. This agar medium is cultured at 37° C. for 3 days, and then the number of mutation colonies is measured. When the number of mutation colonies is increased 2 times or more the negative control and further the increase of the number has dependency on the concentration of the substance tested, the mutagenicity is judged to be positive.

Method for Producing an Aldehyde Gas Deodorant

In the method for producing an aldehyde gas deodorant of the present invention, the deodorant can be produced by mixing together a water-containing inorganic powder, a dihydrazide compound, and water, and removing excess water by a separation method, such as filtration, centrifugal separation, or evaporation. An organic solvent, such as ethanol, may be added in a small amount to the water used in the present invention, but water is preferably solely used. The water-containing inorganic powder and the dihydrazide compound are mixed together and then, water is added to the resultant mixture by dropwise addition or spraying, followed by further mixing, or into the water-containing inorganic powder may be mixed an aqueous solution of the dihydrazide compound by dropwise addition or spraying. The amount of the water used is, relative to 100 parts by mass of the total of the water-containing inorganic powder, the dihydrazide compound, and water, preferably 3 to 70 parts by mass, further preferably 4 to 60 parts by mass. When an aqueous solution of the dihydrazide compound is used, the amount of the water used is, relative to 10 parts by mass of the dihydrazide compound, preferably 3 to 40 parts by mass, further preferably 5 to 30 parts by mass. Mixing is performed using a stirring apparatus, such as a Henschel mixer, at room temperature to lower than 90° C. for several to several tens minutes. The resultant mixture may be further dried at lower than 90° C., preferably at 60° C. to 90° C., more preferably at 60° C. to 80° C., optionally under a reduced pressure.

The dihydrazide compound added together with water is not only merely dried and attached onto the outer surface of the inorganic powder but also supported in the pores of the water-containing inorganic powder upon heating and drying. Therefore, when the drying temperature is lower than 45° C., the dihydrazide compound may be unsatisfactorily supported, and, on the other hand, when the drying temperature is higher than 90° C., the mutagenicity may become positive. When only the dihydrazide compound is heated at 90° C. or higher without the inorganic powder, a phenomenon such that the mutagenicity becomes positive does not occur. Therefore, the reason why the mutagenicity becomes positive is presumed that the dihydrazide compound is decomposed due to a catalytic action of the pore surface of the inorganic powder and changed to a substance which is positive for mutagenicity. However, complete elucidation of the substance formed by a change of the dihydrazide compound and the amount of the substance formed has not yet been made.

The substance formed is not specified, but the present inventors have found a phenomenon such that the dihydrazide compound supported on the inorganic powder is changed to be positive for mutagenicity depending on the conditions, and the present inventor also has found that, in the production of an aldehyde gas deodorant, when the conditions are controlled so that the heating temperature is within the range of from 45° C. to 90° C. and the dried aldehyde gas deodorant has a water content of 4.5% by mass or more, based on the total mass of the aldehyde gas deodorant, an aldehyde gas deodorant which is negative for mutagenicity can be obtained. In the present invention, the lower limit of the water content of the aldehyde gas deodorant is 4.5% or more, and the upper limit is not particularly specified, but is preferably 25% by mass, more preferably 20% by mass.

In the above-mentioned method for producing the aldehyde gas deodorant, the order of addition of the water-containing inorganic powder and the dihydrazide compound may be reversed. Specifically, the aldehyde gas deodorant of the present invention can be produced by stirring an aqueous solution or an aqueous dispersion of the dihydrazide compound at room temperature to lower than 90° C., and adding a water-containing inorganic powder to it and satisfactorily mixing and then, heating and drying the resultant mixture so that the water content becomes 4.5% by mass or more.

In the aldehyde gas deodorant of the present invention, when the amount of the dihydrazide compound supported on the water-containing inorganic powder is increased, the deodorizing effect advantageously tends to become excellent. However, when the amount of the dihydrazide compound supported is too large, the carrier cannot have supported thereon too large an amount of the compound and the deodorizing effect is not further improved. Therefore, the amount of the dihydrazide compound supported is preferably 10 to 90% by mass, further preferably 10 to 50% by mass, especially preferably 10 to 30% by mass, based on the total mass (100% by mass) of the water-containing inorganic powder and the dihydrazide compound. The mass of the water-containing inorganic powder includes the mass of water contained therein.

Mixing with Another Deodorant

The aldehyde gas deodorant of the present invention is effective with respect to aldehyde gas. Examples of aldehyde gases include acetaldehyde, formaldehyde, propanal, butanal, and nonenal. The aldehyde gas deodorant of the present invention and an aldehyde gas deodorant other than the aldehyde gas deodorant of the present invention may be used in combination. Examples of the other aldehyde gas deodorants include ammonium sulfate, polyallylamine hydrochloride, EDTA sodium salt, triethanolamine, pyridine, dimethylhydantoin, casein, urea, thiourea, sodium casein, glycine, hexamethylenetetramine, guanidine nitrate, and hydroxylamine sulfate.

With respect to the method of using the aldehyde gas deodorant of the present invention, the aldehyde gas deodorant is used only for aldehyde gas as an object, and the aldehyde gas deodorant can be mixed with a deodorant for gas other than aldehyde gas (deodorant composition), or can be used in combination with such another deodorant. As a specific example which is mixed with or used in combination with the aldehyde gas deodorant of the present invention, there can be mentioned a basic gas deodorant for deodorizing basic gas, such as ammonia or trimethylamine. As examples of the basic gas deodorants, there can be mentioned tetravalent metal phosphate compounds insoluble in or unlikely to be soluble in water. Specific preferred examples of the tetravalent metal phosphate compounds include zirconium phosphate, titanium phosphate, and tin phosphate. In these compounds, there are those which are crystalline and have various crystal systems, such as an α form crystal, a β form crystal, a γ form crystal, and a NASICON form crystal, and those which are amorphous, and any of the compounds having a gas adsorbing property can be mixed with or used in combination with the aldehyde gas deodorant of the present invention.

Further, the aldehyde gas deodorant of the present invention can be mixed with or used in combination with a sulfur gas deodorant for deodorizing sulfur gas, such as hydrogen sulfide or methylmercaptan. For example, the aldehyde gas deodorant of the present invention can be mixed with or used in combination with a tetravalent metal phosphate compound having supported thereon ions of at least one metal selected from copper, zinc, and manganese, zinc oxide, or zinc silicate. Among the metal ions to be supported on the tetravalent metal phosphate compound, especially preferred are copper ions because high deodorizing effect for hydrogen sulfide or the like is obtained.

For supporting metal ions on the tetravalent metal phosphate compound, the tetravalent metal phosphate compound may be contacted with a solution of a salt of metal ions to support the ions by ion-exchange or the like.

The amount of the metal ions supported can be controlled arbitrarily within the ion-exchange capacity for a tetravalent metal phosphate compound up to 100% if desired.

Further, with respect to zinc oxide, copper silicate, and zinc silicate, preferred is one having a large specific surface area because it has high deodorizing performance.

Further, the aldehyde gas deodorant of the present invention can be mixed with or used in combination with an organic acid gas deodorant for deodorizing malodorous gas, such as acetic acid, isovaleric acid, or butyric acid. For example, a deodorant composition can be obtained by mixing hydrated zirconium oxide or hydrated titanium oxide with the aldehyde gas deodorant of the present invention.

The above-mentioned deodorant or deodorant composition in the present invention is individually obtained generally in a powder form. With respect to the particle diameter of the powder, when subjected to after-processing into thin fibers, the powder having a smaller particle diameter does not adversely affect the texture or hand feeling of the resultant fibers, and further, when added to a molding resin, the powder having a smaller particle diameter advantageously is unlikely to cause the filter in a molding machine to suffer clogging. On the other hand, the powder having a larger particle diameter has excellent dispersibility and hence is unlikely to suffer aggregation. Therefore, with respect to the preferred particle diameter, a median diameter in terms of the volume, as measured by a laser diffraction-type particle size distribution meter, is preferably 0.1 to 100 μm, more preferably 0.5 to 20 μm, yet more preferably 2 to 10 μm.

Further, the aldehyde gas deodorant or deodorant composition of the present invention may be subjected to granulation according to the object of the use. In this case, the deodorant of the present invention and another deodorant may be individually subjected to granulation per component, or the deodorant composition may be subjected to granulation. With respect to the method for producing granules, any method of generally subjecting powder to granulation can be employed. For example, there is a method of obtaining granules using alumina sol, clay, or the like as a binder. The particle diameter can be appropriately controlled according to the hardness and density of the granules, grinding strength, and the like, but, from the viewpoint of easy handling, the particle diameter is preferably 0.1 to 3 mm.

Method for Processing the Aldehyde Gas Deodorant to Obtain a Deodorant Processed Product The deodorant of the present invention can be used in the form of a mixture with a binder resin generally used in a surface treatment for, e.g., an acrylic acid or urethane fiber, nonwoven fabric, sheet, or the like. In this case, if necessary, a dispersant, a surfactant, an anti-foaming agent, a water retention agent, an antiseptic agent, a viscosity modifier, or the like can be added to the mixture, and dispersed by stirring using a sand mill, a disper, a ball mill, or the like. With respect to the ratio between the binder resin and the deodorant mixed, in terms of the solids content, relative to 100 parts by mass of the deodorant, in terms of the solids content, the amount of the binder resin is preferably 10 to 300 parts by mass, in terms of the solids content. When the amount of the binder resin is less than 10 parts by mass, in terms of the solids content, a disadvantage is caused in that when the deodorant dispersion is spread through a fiber, nonwoven fabric, a sheet, or the like, the binding force is unsatisfactory, so that the deodorant is removed, lowering the deodorizing performance. On the other hand, when the amount of the binder resin is more than 300 parts by mass, in terms of the solids content, a disadvantage is caused in that when processed into a fiber, nonwoven fabric, a sheet, or the like, the deodorant is covered by the resin, so that the resultant product does not exhibit satisfactory deodorizing performance.

The aldehyde gas deodorant of the present invention is excellent in aldehyde deodorizing performance and safety, and therefore can be applied to various products, for example, used in a room or a car, which products require the safety, making it possible to reduce harmful aldehyde gas in a living space or the like.

EXAMPLES

Hereinbelow, the present invention will be described in more detail with reference to the following Examples, which should not be construed as limiting the scope of the present invention. "%" indicates % by mass.

In the measurement method for a particle diameter, there was employed a median diameter in terms of the volume determined from the result of a particle size analysis made using a laser diffraction-type particle size distribution meter with respect to the deodorant particles dispersed in deionized water by ultrasonic dispersion. In the measurement of a residual water content, a weight reduction after drying using a dryer at 150° C. for 2 hours was measured.

Measurement of deodorizing effect of a deodorant powder

An aldehyde deodorizing capacity was measured as follows. 0.02 g of a deodorant sample is placed in a vinyl fluoride bag (which is obtained by processing a vinyl fluoride film into a bag form; hereinafter, referred to as "Tedlar bag"), and 2 liters of air containing acetaldehyde gas in an amount of 650 ppm by volume is introduced into the bag, and allowed to stand at room temperature for 2 hours. After 2 hours, an acetaldehyde gas concentration remaining in the Tedlar bag is measured by a gas detector tube (manufactured by Gastec Corporation; hereinafter, the same product is used). A deodorizing capacity was calculated from a value obtained by subtracting the reduction amount measured by a blank test using an empty Tedlar bag from the amount of the gas reduced per g of the deodorant (unit: ml/g; ml indicates a volume of gas in the standard state).

Synthesis Example 1

Synthesis Example of an Amorphous Water-Containing Composite Oxide Represented by the Formula:
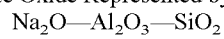

In a 5 L stainless steel reactor was placed 1,360 mL of an aqueous solution containing $Na_2O$ in an amount of 0.52 mol/L and $SiO_2$ in an amount of 1.67 mol/L, and 1,480 mL of a 0.16 mol/L aqueous aluminum sulfate solution was added to the aqueous solution in the reactor using a metering pump over 60 minutes while stirring. A reaction was conducted at 25° C. The resultant reaction mixture was matured by heating at 95° C. for one hour. After maturing, the slurry was subjected to filtration, and washed with deionized water, and dried at 75° C. for 20 hours, followed by pulverization. With respect to the resultant powder, measurement of a water content, measurement of a median diameter in terms of the volume by a laser diffraction-type particle size distribution meter, measurement of a BET method specific surface area by a nitrogen adsorption method, a powder X-ray diffraction analysis, and a compositional analysis were performed. As a result, it was found that the powder was amorphous $0.2Na_2O.Al_2O_3.10SiO_2$ having a water content of 12%, a median diameter of 6 μm, and a specific surface area of 520 $m^2/g$ (sample A).

Synthesis Example 2

Synthesis Example of an Amorphous Water-Containing Composite Oxide Represented by the Formula:
$K_2O$—$Al_2O_3$—$SiO_2$ In a 5 L stainless steel reactor were placed 570 mL of an aqueous solution containing $Na_2O$ in an amount of 0.52 mol/L and $SiO_2$ in an amount of 1.67 mol/L and 420 mL of 2 mol/L potassium hydroxide. To the resultant aqueous solution was added 1,490 mL of a 0.16 mol/L aqueous aluminum sulfate solution at room temperature over 30 minutes while stirring. The resultant reaction mixture was matured at 95° C. for one hour. After maturing, the slurry was subjected to filtration, and washed with deionized water, and dried at 90° C. for 10 hours, followed by pulverization. With respect to the resultant powder, measurement of a water content, measurement of a median diameter in terms of the volume by a laser diffraction-type particle size distribution meter, measurement of a BET method specific surface area by a nitrogen adsorption method, a powder X-ray diffraction analysis, and a compositional analysis were performed. As a result, it was found that the powder was amorphous $0.3K_2O.Al_2O_3.4SiO_2$ having a water content of 9%, a median diameter of 4 μm, and a specific surface area of 430 m²/g (sample B).

Synthesis Example 3

Synthesis Example of an Amorphous Water-Containing Composite Oxide Represented by the Formula:
$Li_2O$—$Na_2O$—$Al_2O_3$—$SiO_2$ In a 5 L stainless steel reactor was placed in advance 800 mL of water, and a 0.16 mol/L aqueous aluminum sulfate solution and an aqueous solution containing $Li_2O$ in an amount of 0.20 mol/L, $Na_2O$ in an amount of 0.40 mol/L, and $SiO_2$ in an amount of 1.67 mol/L were simultaneously added dropwise to the water at room temperature while stirring. The resultant reaction mixture was matured at 85° C. for one hour. After maturing, the slurry was subjected to filtration, and washed with deionized water, and dried at 80° C. for 10 hours, followed by pulverization. With respect to the resultant powder, measurement of a water content, measurement of a median diameter in terms of the volume by a laser diffraction-type particle size distribution meter, measurement of a BET method specific surface area by a nitrogen adsorption method, a powder X-ray diffraction analysis, and a compositional analysis were performed. As a result, it was found that the powder was amorphous $0.1Li_2O.0.2Na_2O.Al_2O_3.9SiO_2$ having a water content of 9%, a median diameter of 10 μm, and a specific surface area of 360 m²/g (sample C).

Example 1

20 g of adipic dihydrazide and 80 g of the water-containing inorganic powder sample A were mixed together, and 20 g of deionized water was further added thereto and mixed for one hour. The resultant mixture was dried by a dryer at 65° C. for 3 hours. With respect to the powder obtained after drying, measurement of a residual water content, a mutagenicity test, and measurement of an aldehyde deodorizing capacity were performed, and the results were shown in Table 2.

Example 2

25 g of adipic dihydrazide and 75 g of the water-containing inorganic powder sample A were mixed together, and 20 g of deionized water was further added thereto and mixed for 30 minutes. The resultant mixture was dried by a dryer at 80° C. for one hour. With respect to the powder obtained after drying, measurement of a residual water content, a mutagenicity test, and measurement of an aldehyde deodorizing capacity were performed, and the results were shown in Table 2.

Example 3

15 g of adipic dihydrazide and 85 g of the water-containing inorganic powder sample B were mixed together, and 10 g of deionized water was further added thereto and mixed for 30 minutes. The resultant mixture was dried by a dryer at 85° C. for 30 minutes. With respect to the powder obtained after drying, measurement of a residual water content, a mutagenicity test, and measurement of an aldehyde deodorizing capacity were performed, and the results were shown in Table 2.

Example 4

20 g of adipic dihydrazide and 80 g of the water-containing inorganic powder sample A were mixed together, and 20 g of deionized water was further added thereto and mixed for 12 minutes. The resultant mixture was dried by a dryer at 50° C. for 4 hours. With respect to the powder obtained after drying, measurement of a residual water content, a mutagenicity test, and measurement of an aldehyde deodorizing capacity were performed, and the results were shown in Table 2.

Example 5

20 g of adipic dihydrazide and 80 g of silica gel having a water content of 13%, a specific surface area of 500 m²/g, and a median diameter of 4 μm were mixed together, and 20 g of deionized water was further added thereto and mixed for 6 minutes. The resultant mixture was dried by a dryer at 75° C. for 2 hours. With respect to the powder obtained after drying, measurement of a residual water content, a mutagenicity test, and measurement of an aldehyde deodorizing capacity were performed, and the results were shown in Table 2.

Example 6

12 g of succinic dihydrazide and 88 g of the water-containing inorganic powder sample A were mixed together, and 10 g of deionized water was further added thereto and mixed for 12 minutes. The resultant mixture was dried by a dryer at 80° C. for 2 hours. With respect to the powder obtained after drying, measurement of a residual water content, a mutagenicity test, and measurement of an aldehyde deodorizing capacity were performed, and the results were shown in Table 2.

Example 7

20 g of carbodihydrazide and 80 g of the water-containing inorganic powder sample C were mixed together, and 20 g of deionized water was further added thereto and mixed for 12 minutes. The resultant mixture was dried by a dryer at 90° C. for one hour. With respect to the powder obtained after drying, measurement of a residual water content, a mutagenicity test, and measurement of an aldehyde deodorizing capacity were performed, and the results were shown in Table 2.

Example 8

20 g of isophthalic dihydrazide and 80 g of the water-containing inorganic powder sample A were mixed together, and 50 g of deionized water was further added thereto and mixed for 12 minutes. The resultant mixture was dried by a dryer at 90° C. for one hour. With respect to the powder obtained after drying, measurement of a residual water content, a mutagenicity test, and measurement of an aldehyde deodorizing capacity were performed, and the results were shown in Table 2.

Comparative Example 1

15 g of hydrazine hydrate and 85 g of the water-containing inorganic powder sample A were mixed together, and 5 g of deionized water was further added thereto and mixed for 12 minutes. The resultant mixture was air-dried. With respect to the powder obtained after drying, measurement of a residual water content, a mutagenicity test, and measurement of an aldehyde deodorizing capacity were performed, and the results were shown in Table 2.

Comparative Example 2

20 g of succinic dihydrazide and 80 g of the water-containing inorganic powder sample A were mixed together, and 10 g of deionized water was further added thereto and mixed for 30 minutes. The resultant mixture was dried at 140° C. for 3 hours. With respect to the powder obtained after drying, measurement of a residual water content, a mutagenicity test, and measurement of an aldehyde deodorizing capacity were performed, and the results were shown in Table 2.

Comparative Example 3

12 g of succinic dihydrazide and 88 g of anhydrous alumina silica powder were mixed together, and 10 g of deionized water was further added thereto and mixed for 30 minutes. The resultant mixture was dried at 140° C. for 3 hours. With respect to the powder obtained after drying, measurement of a residual water content, a mutagenicity test, and measurement of an aldehyde deodorizing capacity were performed, and the results were shown in Table 2.

Comparative Example 4

7 g of succinic dihydrazide and 93 g of anhydrous alumina silica were mixed together, and 10 g of deionized water was further added thereto and mixed for 12 minutes. The resultant mixture was dried at 50° C. for 10 hours. With respect to the powder obtained after drying, measurement of a residual water content, a mutagenicity test, and measurement of an aldehyde deodorizing capacity were performed, and the results were shown in Table 2.

Comparative Example 5

20 g of carbodihydrazide and 80 g of the water-containing inorganic powder sample C were mixed together, and 20 g of deionized water was further added thereto and mixed for 30 minutes. The resultant mixture was dried at 120° C. for 4 hours. With respect to the powder obtained after drying, measurement of a residual water content, a mutagenicity test, and measurement of an aldehyde deodorizing capacity were performed, and the results were shown in Table 2.

Comparative Example 6

20 g of adipic dihydrazide and 80 g of the water-containing inorganic powder sample A were mixed together, and 20 g of deionized water was further added thereto and mixed for 30 minutes. The resultant mixture was dried at 100° C. for 1.5 hour. With respect to the powder obtained after drying, measurement of a residual water content, a mutagenicity test, and measurement of an aldehyde deodorizing capacity were performed, and the results were shown in Table 2.

Comparative Example 7

8 g of adipic dihydrazide and 92 g of the water-containing inorganic powder sample B were mixed together, and 20 g of deionized water was further added thereto and mixed for 12 minutes. The resultant mixture was dried at 100° C. for 1.5 hour. With respect to the powder obtained after drying, measurement of a residual water content, a mutagenicity test, and measurement of an aldehyde deodorizing capacity were performed, and the results were shown in Table 2.

Comparative Example 8

8 g of adipic dihydrazide and 92 g of anhydrous alumina silica were mixed together, and 5 g of deionized water was further added thereto and mixed for 12 minutes. The resultant mixture was dried at 65° C. for 2 hours. With respect to the powder obtained after drying, measurement of a residual water content, a mutagenicity test, and measurement of an aldehyde deodorizing capacity were performed, and the results were shown in Table 2.

Comparative Example 9

8 g of adipic dihydrazide and 92 g of the water-containing inorganic powder sample B were mixed together, and 20 g of deionized water was further added thereto and mixed for 12 minutes. The resultant mixture was dried at 100° C. for 1.5 hour. With respect to the powder obtained after drying, measurement of a residual water content, a mutagenicity test, and measurement of an aldehyde deodorizing capacity were performed, and the results were shown in Table 2.

Comparative Example 10

20 g of adipic dihydrazide and 80 g of the water-containing inorganic powder sample C were mixed together, and 20 g of deionized water was further added thereto and mixed for 12 minutes. The resultant mixture was dried at 95° C. for 3 hours. With respect to the powder obtained after drying, measurement of a residual water content, a mutagenicity test, and measurement of an aldehyde deodorizing capacity were performed, and the results were shown in Table 2.

Comparative Example 11

20 g of adipic dihydrazide and 80 g of anhydrous crystalline aluminosilicate were mixed together, and 20 g of deionized water was further added thereto and mixed for 12 minutes. The resultant mixture was dried at 80° C. for 2 hours. With respect to the powder obtained after drying, measurement of a residual water content, a mutagenicity test, and measurement of an aldehyde deodorizing capacity were performed, and the results were shown in Table 2.

Comparative Example 12

20 g of adipic dihydrazide and 80 g of anhydrous amorphous magnesium silicate were mixed together, and 20 g of deionized water was further added thereto and mixed for 12 minutes. The resultant mixture was dried at 75° C. for 2 hours. With respect to the powder obtained after drying, measurement of a residual water content, a mutagenicity test, and measurement of an aldehyde deodorizing capacity were performed, and the results were shown in Table 2.

Comparative Example 13

20 g of adipic dihydrazide and 80 g of anhydrous silica were mixed together, and 20 g of deionized water was further added thereto and mixed for 12 minutes. The resultant mixture was dried at 65° C. for 2 hours. With respect to the powder obtained after drying, measurement of a residual water content, a mutagenicity test, and measurement of an aldehyde deodorizing capacity were performed, and the results were shown in Table 2.

Comparative Example 14

20 g of adipic dihydrazide and 80 g of anhydrous silica were mixed together, and 10 g of deionized water was further added thereto and mixed for 30 minutes. The resultant mixture was dried at 120° C. for 3 hours. With respect to the powder obtained after drying, measurement of a residual water content, a mutagenicity test, and measurement of an aldehyde deodorizing capacity were performed, and the results were shown in Table 2.

TABLE 1

| | Deodorant | Parts by mass | Inorganic carrier | Parts by mass | Water | Mixing time (hr) | Heating temperature (° C.) | Heating time (hr) |
|---|---|---|---|---|---|---|---|---|
| Example 1 | Adipic dihydrazide | 20 | Sample A | 80 | 20 | 1 | 65 | 3 |
| Example 2 | Adipic dihydrazide | 25 | Sample A | 75 | 20 | 0.5 | 80 | 1 |
| Example 3 | Adipic dihydrazide | 15 | Sample B | 85 | 10 | 0.5 | 85 | 0.5 |
| Example 4 | Adipic dihydrazide | 20 | Sample A | 80 | 20 | 0.2 | 50 | 4 |
| Example 5 | Adipic dihydrazide | 20 | Silica gel | 80 | 20 | 0.1 | 75 | 2 |
| Example 6 | Succinic dihydrazide | 12 | Sample A | 88 | 10 | 0.2 | 80 | 2 |
| Example 7 | Carbo-dihydrazide | 20 | Sample C | 80 | 20 | 0.2 | 90 | 1 |
| Example 8 | Isophthalic dihydrazide | 20 | Sample A | 80 | 50 | 0.2 | 90 | 1 |
| Comparative Example 1 | Hydrazine hydrate | 15 | Sample A | 85 | 5 | 0.2 | 25 | 3 |
| Comparative Example 2 | Succinic dihydrazide | 20 | Sample A | 80 | 10 | 0.5 | 140 | 3 |
| Comparative Example 3 | Succinic dihydrazide | 12 | Anhydrous alumina silica | 88 | 10 | 0.5 | 140 | 3 |
| Comparative Example 4 | Succinic dihydrazide | 7 | Anhydrous alumina silica | 93 | 10 | 0.2 | 50 | 10 |
| Comparative Example 5 | Carbo-dihydrazide | 20 | Sample C | 80 | 20 | 0.5 | 120 | 4 |
| Comparative Example 6 | Adipic dihydrazide | 20 | Sample A | 80 | 20 | 0.5 | 100 | 1.5 |
| Comparative Example 7 | Adipic dihydrazide | 8 | Sample B | 92 | 20 | 0.2 | 100 | 1.5 |
| Comparative Example 8 | Adipic dihydrazide | 8 | Anhydrous alumina silica | 92 | 5 | 0.2 | 65 | 2 |
| Comparative Example 9 | Adipic dihydrazide | 8 | Sample B | 92 | 20 | 0.2 | 100 | 1.5 |
| Comparative Example 10 | Adipic dihydrazide | 20 | Sample C | 80 | 20 | 0.2 | 95 | 3 |
| Comparative Example 11 | Adipic dihydrazide | 20 | Anhydrous crystalline aluminosilicate | 80 | 20 | 0.2 | 80 | 2 |
| Comparative Example 12 | Adipic dihydrazide | 20 | Anhydrous amorphous magnesium silicate | 80 | 20 | 0.2 | 75 | 2 |
| Comparative Example 13 | Adipic dihydrazide | 20 | Anhydrous silica | 80 | 20 | 0.2 | 65 | 2 |
| Comparative Example 14 | Adipic dihydrazide | 20 | Anhydrous silica | 80 | 10 | 0.5 | 120 | 3 |

TABLE 2

| | Deodorant | Inorganic carrier | Heating temperature (° C.) | Residual water content (%) | Mutagenicity | Deodorizing capacity (ml/g) |
|---|---|---|---|---|---|---|
| Example 1 | Adipic dihydrazide | Sample A | 65 | 9.8 | Negative | 34 |
| Example 2 | Adipic dihydrazide | Sample A | 80 | 8 | Negative | 40 |
| Example 3 | Adipic dihydrazide | Sample B | 85 | 5.8 | Negative | 32 |

TABLE 2-continued

| | Deodorant | Inorganic carrier | Heating temperature (° C.) | Residual water content (%) | Mutagenicity | Deodorizing capacity (ml/g) |
|---|---|---|---|---|---|---|
| Example 4 | Adipic dihydrazide | Sample A | 50 | 14.5 | Negative | 27 |
| Example 5 | Adipic dihydrazide | Silica gel | 75 | 7.4 | Negative | 24 |
| Example 6 | Succinic dihydrazide | Sample A | 80 | 6.2 | Negative | 28 |
| Example 7 | Carbo-dihydrazide | Sample C | 90 | 9.5 | Negative | 26 |
| Example 8 | Isophthalic dihydrazide | Sample A | 90 | 5.2 | Negative | 26 |
| Comparative Example 1 | Hydrazine hydrate | Sample A | 25 | 8.6 | Positive | 38 |
| Comparative Example 2 | Succinic dihydrazide | Sample A | 140 | 1.2 | Positive | 47 |
| Comparative Example 3 | Succinic dihydrazide | Anhydrous alumina silica | 140 | 0.9 | Positive | 28 |
| Comparative Example 4 | Succinic dihydrazide | Anhydrous alumina silica | 50 | 9.2 | Negative | 11 |
| Comparative Example 5 | Carbo-dihydrazide | Sample C | 120 | 1.7 | Positive | 34 |
| Comparative Example 6 | Adipic dihydrazide | Sample A | 100 | 3.3 | Positive | 35 |
| Comparative Example 7 | Adipic dihydrazide | Sample B | 100 | 2.6 | Positive | 18 |
| Comparative Example 8 | Adipic dihydrazide | Anhydrous alumina silica | 65 | 5.5 | Negative | 9 |
| Comparative Example 9 | Adipic dihydrazide | Sample B | 100 | 0.8 | Positive | 14 |
| Comparative Example 10 | Adipic dihydrazide | Sample C | 95 | 1.5 | Positive | 16 |
| Comparative Example 11 | Adipic dihydrazide | Anhydrous crystalline aluminosilicate | 80 | 6 | Negative | 17 |
| Comparative Example 12 | Adipic dihydrazide | Anhydrous amorphous magnesium silicate | 75 | 8.2 | Negative | 19 |
| Comparative Example 13 | Adipic dihydrazide | Anhydrous silica | 65 | 9.8 | Negative | 13 |
| Comparative Example 14 | Adipic dihydrazide | Anhydrous silica | 120 | 2.1 | Positive | 42 |

The results shown in Table 2 indicate that, in Examples 1 to 8 corresponding to the aldehyde gas deodorant of the present invention, not only is the mutagenicity negative, but also the deodorizing capacity is large and the deodorizing performance with respect to aldehyde is high.

With respect to the aldehyde gas deodorant using hydrated hydrazine which is strongly positive for mutagenicity, even when the deodorant was not subjected to heating treatment, the mutagenicity was positive (Comparative Example 1). With respect to the aldehyde gas deodorant which has succinic dihydrazide supported and has a water content reduced to less than 4.5% by mass by a heating treatment, high deodorizing capacity can be obtained even when the amount of the succinic dihydrazide supported is slightly small, but the mutagenicity is positive (Comparative Examples 2 and 3). With respect to the aldehyde gas deodorant which has supported carbohydrazide and adipic dihydrazide, which are negative for mutagenicity, and has a water content reduced to less than 4.5% by mass by a heating treatment at a temperature of higher than 90° C., the deodorizing capacity was exhibited, but the mutagenicity was positive (Comparative Examples 5, 6, 7, 9, 10, and 14). In Comparative Examples 11, 12, and 13 in which an anhydrous inorganic carrier was used and a heating treatment in the range of from 60 to 90° C. was performed so that the residual water content became more than 4.5% by mass, the mutagenicity was negative, but the deodorizing capacity was apparently small, as compared to that in Examples 1, 4, and 5 in which a dihydrazide compound in an amount of 20% by mass was supported. In Comparative Examples 4 and 8 in which an anhydrous inorganic carrier was used and a heating treatment at lower than 60° C. or in the range of from 60° C. to 90° C. was performed, the mutagenicity was negative, but the deodorizing capacity was small.

Specifically, the aldehyde gas deodorant produced by the method disclosed in the present invention has a characteristic feature such that the aldehyde gas deodorant is negative for mutagenicity and has high deodorizing performance with respect to aldehyde gas, and an aldehyde gas deodorant produced by a method other than the method of the present invention has high deodorizing performance with respect to aldehyde gas but is positive for mutagenicity, or is negative for mutagenicity but has poor deodorizing performance with respect to aldehyde gas, or is positive for mutagenicity and has poor deodorizing performance, and these results have confirmed that the deodorant of the present invention is excellent in the aldehyde deodorization use in which the mutagenicity is required to be negative.

Example 9

Preparation of Deodorizing Nonwoven Fabric

To 100 parts by mass of deionized water were added 10 parts by mass of the aldehyde gas deodorant in Example 1 and 3 parts by mass of an acrylic binder (KB-1300, manufactured by Toagosei Co., Ltd.) to prepare a suspension. 50 Parts by mass of the prepared suspension was applied to 100 parts by mass of polyester nonwoven fabric, and dried at 110° C. to obtain deodorizing nonwoven fabric a (in which the amount of the deodorant contained was 1.5 part by mass, relative to 100 parts by mass of the resin).

Comparative Example 15

Deodorizing nonwoven fabric b was obtained in accordance with substantially the same procedure as in Example 9 except that the aldehyde gas deodorant in Comparative Example 13 was used.

Comparative Example 16

Unprocessed nonwoven fabric, which uses no aldehyde gas deodorant and is not processed with a binder, was subjected to measurement of deodorizing effect in Comparative Example 16.

Measurement of Deodorizing Effect with Respect to Deodorizing Nonwoven Fabric a, b and Unprocessed Nonwoven Fabric Each deodorizing nonwoven fabric cut into 10 cm×10 cm was placed in a Tedlar bag, and 1 liter of air containing acetaldehyde gas in an amount of 20 ppm by volume was introduced into the bag, and allowed to stand at room temperature. After 2 hours, the aldehyde gas remaining in the Tedlar bag was collected by a cartridge for collecting aldehydes and ketones (manufactured by GL Science Inc.), and the collected aldehyde was dissolved in acetonitrile and subjected to measurement by high performance liquid chromatography (manufactured by Shimadzu Corporation) to determine a residual aldehyde concentration. A reduction ratio (%) of the residual acetaldehyde concentration to the initial concentration was calculated as a deodorization rate. The results are shown in Table 3.

TABLE 3

|  | Nonwoven fabric | Deodorant | Deodorization rate |
| --- | --- | --- | --- |
| Example 9 | Deodorizing nonwoven fabric a | Example 1 | 99.9% or more |
| Comparative Example 15 | Deodorizing nonwoven fabric b | Comparative Example 13 | 98% |
| Comparative Example 16 | Unprocessed nonwoven fabric | None | 10% or less |

The results have confirmed that when producing a deodorant processed product using the aldehyde gas deodorant of the present invention, there can be obtained a product which is negative for mutagenicity and which has high deodorizing performance with respect to aldehyde. Specifically, it is apparent that a deodorant processed product obtained by processing the aldehyde gas deodorant of the present invention achieves safety when used in the application in which the product is possibly in contact with a human body in a living space, and further exhibits excellent deodorizing performance with respect to aldehyde gas.

INDUSTRIAL APPLICABILITY

The aldehyde gas deodorant of the present invention is excellent in aldehyde deodorizing performance and safety, and therefore, when the aldehyde gas deodorant is applied to various products used in a room, a car, or the like, which products need to care about the safety, aldehyde gas can be reduced.

What is claimed is:

1. A method for producing an aldehyde gas deodorant comprising the steps of:
   preparing a deodorizing composition containing a dihydrazide compound, a water-containing inorganic powder, and water; and
   heating the deodorizing composition at a temperature of from 45° C. to 90° C. so that water remains in an amount of 4.5% by mass or more, based on the total mass of the deodorant produced, and
   wherein the aldehyde gas deodorant is negative for mutagenicity measured by an AMES test.

2. The method for producing an aldehyde gas deodorant according to claim 1, wherein the dihydrazide compound is represented by the formula (1) below:

$$H_2NHN-X-NHNH_2 \tag{1}$$

wherein X represents a group (—CO—) or a group (—CO-A-CO—) wherein A represents an alkylene group having 1 to 16 carbon atoms or an arylene group having 6 to 12 carbon atoms.

3. The method for producing an aldehyde gas deodorant according to claim 1, wherein the dihydrazide compound is at least one selected from the group consisting of carbohydrazide, succinic dihydrazide, adipic dihydrazide, and isophthalic dihydrazide.

4. The method for producing an aldehyde gas deodorant according to claim 1, wherein the water-containing inorganic powder independently has a water content of 3 to 25% by mass under 1 atm at 25° C.

5. The method for producing an aldehyde gas deodorant according to claim 1, wherein the water-containing inorganic powder is amorphous.

6. The method for producing an aldehyde gas deodorant according to claim 1, wherein the water-containing inorganic powder is an amorphous composite oxide.

7. The method for producing an aldehyde gas deodorant according to claim 1, wherein the water-containing inorganic powder is a composite oxide containing an oxide selected from the group consisting of $Al_2O_3$, $SiO_2$, MgO, CaO, SrO, BaO, ZnO, $ZrO_2$, $TiO_2$, $WO_2$, $CeO_2$, $Li_2O$, $Na_2O$, and $K_2O$.

8. The method for producing an aldehyde gas deodorant according to claim 1, wherein the water-containing inorganic powder comprises the formula: $X_2O$—$Al_2O_3$—$SiO_2$, wherein X represents at least one alkali metal selected from Na, K, and Li.

9. The method for producing an aldehyde gas deodorant according to claim 1, wherein the amount of the dihydrazide supported is 10 to 90% by mass, based on the total mass of the dihydrazide compound and the water-containing inorganic powder.

10. The method for producing an aldehyde gas deodorant according to claim 1, wherein the dihydrazide compound comprises adipic dihydrazide.

11. An aldehyde gas deodorant which is obtained by the method according to claim 1.

12. A deodorant processed product comprising the aldehyde gas deodorant according to claim 11.

13. The deodorant processed product according to claim 12, which is selected from the group consisting of a fiber, a coating composition, a sheet, and a shaped article.

14. The deodorant processed product according to claim 13, which is obtained by subjecting the aldehyde gas deodorant to after-processing using a binder.

* * * * *